(12) United States Patent
Kim et al.

(10) Patent No.: US 8,394,426 B2
(45) Date of Patent: Mar. 12, 2013

(54) COMPOSITION COMPRISING AN EXTRACT OF HARDY KIWI FOR PREVENTING OR TREATING BALDNESS DISORDERS OR SEBORRHEIC SKIN DISORDERS

(75) Inventors: Bongcheol Kim, Gwacheon-si (KR); Hwa-Jun Lee, Suwon-si (KR); Mirim Jin, Seoul (KR); Hyung-Jin Jung, Seoul (KR); Sunyoung Kim, Seoul (KR)

(73) Assignee: Viromed Co., Ltd., Seoul (KR)

( * ) Notice: Subject to any disclaimer, the term of this patent is extended or adjusted under 35 U.S.C. 154(b) by 0 days.

(21) Appl. No.: 12/868,130

(22) Filed: Aug. 25, 2010

(65) Prior Publication Data

US 2010/0330214 A1    Dec. 30, 2010

Related U.S. Application Data

(63) Continuation-in-part of application No. 11/573,445, filed as application No. PCT/KR2004/002010 on Aug. 10, 2004, now abandoned.

(51) Int. Cl.
*A61K 36/00* (2006.01)
(52) U.S. Cl. ........................................... 424/725
(58) Field of Classification Search .................. 424/725
See application file for complete search history.

(56) References Cited

FOREIGN PATENT DOCUMENTS

| | | |
|---|---|---|
| CN | 1195548 A | 10/1998 |
| EP | 0 383 437 A2 | 8/1990 |
| EP | 0569667 A2 | 11/1993 |
| JP | 61-140510 A | 6/1986 |
| JP | 02-006403 A | 1/1990 |
| JP | 02-276561 A | 11/1990 |
| JP | 02-282314 A | 11/1990 |
| JP | 06-247831 A | 9/1994 |
| JP | 10-182475 A | 7/1998 |
| JP | 2001-220344 A | 8/2001 |
| JP | 2002-173416 A | 6/2002 |
| JP | 2003-176213 A | 6/2003 |
| KR | 2004-0097716 A | 11/2004 |
| WO | 02/069992 A1 | 9/2002 |

OTHER PUBLICATIONS

Chemist & Druggist, London: Hair-Rasing Problems, (1998) p. V, pp. 1-5 of ProQuest.*
Johnson et al. Treatment of Seborrheic Dermatitis; American Family Physician, May 1, 2000; vol. 61, Issue 9, p. 2703, pp. 1-5 of ProQuest.*
MacDonald et al.: Supporting Patients With Alopecia, Practice Nurse, May 11, 2007; 33, 9; ProQuest Nursing & Allied health Source, pp. 46, 48 and 50.*
Minciotti, H. Dr, Simple Treatments Can Reduce the Symptoms of Cradle Cap; Daily Herald, Arlington Heights, Ill.: Nov. 24, 2008, p. 4, pp. 1-2 of Proques.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Ferriss, L. The Vine's Sublime But These Hardy Kiwis Are Even Better; Portland Press Herald, Portland, Me, Sep. 7, 1997, p. 4G (pp. 1-2 from Proquest database provided).*

(Continued)

*Primary Examiner* — Patricia Leith
(74) *Attorney, Agent, or Firm* — Sughrue Mion, PLLC

(57) ABSTRACT

The present invention relates to a use of a crude extract, non-polar solvent soluble extract or purified extract of the hardy kiwifruit for the preparation of therapeutic agent for treating and preventing baldness disorder and seborrheic skin disease in human and mammal, and health care food, food additives, feed additives, cosmetic composition comprising the same. The hardy kiwifruit reduced blood DHT level, promoted the formation of hair root in mouse model experiment, and inhibited the falling out of hair and improved seborrheic skin disease of volunteers such as keratigenous skin, seborrhea etc.

5 Claims, 6 Drawing Sheets

OTHER PUBLICATIONS

Smith, CG: More Than a Mouthful; Sunday times, London (UK), Jun. 10, 2001, p. 26 (pp. 1-4 of ProQuest database print-out provided).*

Japanese Office Action issued in corresponding JP Application No. 2007-525527, dated Aug. 31, 2010.

Bergbrant et al., "Cell-mediated Immunity to *Malassezia furfur* in Patiends with Seborrhoeic Dermatitis and Pityriasis Versicolor," 1999, Clinical and Experimental Dermatology, vol. 24, pp. 402-406.

Faergemann et al., "Seborrhoeic Dermatitis and Pityrosporum (*Malassezia*) Folliculitis: Characterization of Inflammatory Cells and Mediators in the Skin by Immunohistochemistry," 2001, British Journal of Dermatology, vol. 144, pp. 549-556.

Mandt et al., "Interleukin-4 Induces Apoptosis in Cultured Human Follicular Keratinocytes, But Not in Dermal Papilla Cells," 2002, Eur. J. Dermatol., vol. 12, No. 5, Abstract.

Neuber et al., "Effects of Pityrosporum Ovale on Prolideration, Immunoglobulin (IgA, G, M) Synthesis and Cytokine (IL-2, IL-10, IFNγ) Production of Peripheral Blood Mononuclear Cells from Patients with Seborrhoeic Dermatitis," 1996, Arch. Dermatol. Res., vol. 288, pp. 532-536.

Parry et al., "Seborrhoeic Dermatitis is Not Caused by an Altered Immune Response to *Malassezia* Yeast," 1998, British Journal of Dermatology, vol. 139, pp. 254-263.

Strik et al., "'Ananasnaya' Hardy Kiwifruit," 2006, Journal of the American Pomological Society, Abstract.

Jin et al., "Chemical Constituents of Accindia Argula Roots," 1998, Chinese Pharmaceutical Journal, vol. 33, No. 7, pp. 402-404.

Chemical Abstracts, AN, 1990:175690.

Abshee et al., "Cell-mediated Immune Responses to Furfur Serovars A, B and C in Patients with Pityriasis Versicolor, Seborrhoeic Determatitis and Controls," 1994, Exp. Dermatol., vol. 3, No. 3, Abstract.

Bergbrant et al., "An Immunological Study in Patients with Seborrhoeic Dermatitis," 1991, Clin. Exp. Dermatol., vol. 16, No. 5, Abstract.

Jarrousse et al., "Identification of Clustered Cells in Human Hair Follicle Responsible for MMP-9 Gelatinolytic Activity: Consequences for the Regulation of Hair Growth," International Journal of Dermatology, 2001, vol. 40, No. 6, pp. 385-392.

Japanese Patent Office, Japanese Office Action issued in corresponding JP Application No. 2007-525527, dated May 24, 2011.

Chemist & Druggist, London: Hair-Raising Problems, (1998) p. V, pp. 1-5 of ProQuest.

Johnson et al. Treatment of Seborrheic Dermatitis; American Family Physician, May 1, 2000; vol. 61, Issue 9, p. 2703, pp. 1-5 ProQuest.

MacDonald et al.: Supporting Patients With Alopecia, Practice Nurse, May 11, 2007; 33, 9; ProQuest Nursing & Allied health Source, pp. 46-50.

Minciotti, H. Dr, Simple Treatments Can Reduce the Symptoms of Cradle Cap; Daily Hearld, Arlington Heights, Ill.: Nov. 24, 2008, p. 4, pp. 1-2 of Proquest.

European Office Action for European Patent Application No. 04 774 293.7; mailed Oct. 27, 2010.

* cited by examiner

COMPOSITION COMPRISING AN EXTRACT OF HARDY KIWI FOR PREVENTING OR TREATING BALDNESS DISORDERS OR SEBORRHEIC SKIN DISORDERS

This application is a continuation-in-part application of U.S. application Ser. No. 11/573,445 filed on Feb. 8, 2007, which is a national stage application under 35 U.S.C. §371 of PCT/KR2004/002010 filed on Aug. 10, 2004, the disclosures of which are incorporated herein by reference.

BACKGROUND OF THE INVENTION

1. Technical Field

The present invention relates to a composition comprising an extract of hardy kiwi having preventing, improving or treating activity of baldness disorder or seborrheic skin disease.

2. Background Art

The present invention relates to a composition comprising the extract of hardy kiwi having ability of preventing and treating on baldness disease or seborrheic skin disease, and especially, a composition comprising a crude extract, non-polar solvent soluble extract, or purified fraction of hardy kiwi extract for the prevention or treatment of baldness disease or seborrheic skin disease.

Baldness syndrome is frequently occurred in middle-aged male and classified into two types of baldness. One is male pattern baldness alternatively named as an alopecia seniles or androgenic alopecia generally occurred in the forehead or calvaria of middle-aged male, and another is alopecia areata which shows relatively concrete border line of alopecia and frequently being occurred in juvenile person. The syndrome is mainly occurred in male and even in female (M. Inaba et al; Androgenetic alopecia, Springer-Berlag, Tokyo, Japan, 1996).

There has been reported that alopecia is originated from genetic factor, the progress of aging, drug abuse, radioactive treatment and the stress occurred after serious illness etc. It has been known that main factors of alopecia are over-production of androgenic hormone, blood circulation problem in scalp, and deficiency of essential vitamins to hair metabolism in biochemical and physiological aspects. The main factor of male pattern baldness relates to androgen and steroid hormones, in particular, 5-α-reductase which is converting testosterone to 5-α-dihydrotestosterone (DHT) and which is distributed in sebaceous gland, keratinocytes of hair follicle, dermal papilla cell, sweat gland, root sheath of the scalp hair follicle and aromatase which is converting androgen to female hormone such as estradiol. The etiological origin of alopecia greata is known to be the disorder of autoimmune system, especially the lymphocyte CD4+ disorder in melanocyte, keratinocyte, dermal papilla and vascular endothelium (J. Shapiro et al; Therapeutic agents, *Dermatol. Clin.*, 16(2) pp 341-356, 1998).

Various conventional drugs for the treatment of alopecia have been developed till now. Finasteride, an oral 5-α-reductase inhibitor, is available in the market, however it has several disadvantages such as recurrence at cease of administration, usage limitation in pregnant women, and sexual dysfunction upon long-term administration; minoxidil has been used to treat male pattern baldness combined with other agents such as cell division accelerator, vasodilator, capillary formation promotor, immuno-suppressor, cAMP modulator, EGF(epithelial cell growth factor), and cell proliferation modulator. However it also has adverse effects such as repetitive recurrence and rapid reduction of blood pressure at cease of administration too. ACTH (adrenocorticotrophin) an immuno-modulating agent acting on limphocyte to suppress hyperactive immune system has been administrated to treat alopecia greata in forms of ointment or in injection formulations. However it also has several disadvantages including recurrence and adverse effects upon long term administration. Besides the described drugs, cyproterone actate, spironolactone or estrogen have been reported to treat alopecia (J. Shapiro et al, Hair regrowth, Therapeutic agents, *Dermatol. Clin.* 16(2), pp 341-356, 1998)

Most of them do not provide enough efficacy to accomplish a satisfactory activity and have several disadvantages including recurrence and adverse effects. Therefore there have been demands for a new drug which provides with satisfactory effect and reduced adverse effect till now.

Meanwhile, there have been various approaches to develop an effective drug from natural resources to treat and to prevent alopecia.

As an alternative approach, there have been several reports on a composition comprising an extract of natural product having hair growth stimulating effect, for example, 1) an extract belonged to Orchidaceae disclosed in Korea Patent Registration No. 015667; 2) vitex seed and bear fat in Korea Patent Registration No. 0161338; 3) an extract of *Rhododendron fauriae* in Korea Patent Publication No. 91-106; 4) pine leaf extract in Korea Patent Publication No. 96-40346; 5) a crude extract of torilla seed, pine leaf and silkworm moth in Korea Patent Publication No. 90-2757; 6) a crude extract of *Acanthopanax sessiliflorus, Astragalus membranceus, Polygonum multiflorum, Dioscorea nipponica* and *Fagopyrum esculentum* in Korea Patent Publication No. 2000-24499; 7) a crude extract of *Pinellia ternata, Eugenia Caryophyllata, Rubus coreanus, Zanthoxylum piperatum, Vitex rotundifolia, Salvia miltiorrhiza*, and *Thujae semen* in Korea Patent Registration No. 259037; 8) the fat obtained by heating silkworm and their byproduct, at 200° C. for 15 mins, an extract of one or more of *Panax ginseng, Angelica sinensis, Astragalus membranceus, Polygonum multiflorum, Juglans sinensis, Rubus coreanus, Rehmannia glustinosa, Psoralea corylifolia, Pinus densiflora, Vitex rotundifolia, Carthamus tinctorius* and *Ligustrum lucidum* in Korea Patent Publication No. 90-13934; 9) an extract of one or more of silkworm moth, silkworm eggs, silkworm pupa, black sesame seeds, sesame seeds, brown seaweed, and walnuts in Korea Patent Publication No. 90-5952; 10) mixed powder of mung beans, soy bean, perilla seeds, sesame seeds, walnuts, layer, sea mussel, oyster, anchovy, brown seaweed, and yeast concentrates in Korea Patent Registration No. 260673; and 11) an extract of fruits, root, branch, leaf, flowers of *Lycium chinensis*, and corn silk in Korea Patent Publication No. 2000-36534. However, the hair growing effect of the above described composition disclosed therein have not been fully supported or identified in any of the disclosure.

More than 30 species belonged to Actinidiaceae have been reported. *Actinidia arguta, A. polygama* and *A. kolomikta* belonged to Actinidiaceae, are distributed in Siberia, the northern area of China, North and South Korea. *Actinidia arguta, A. polygama* and *A. kolomikta* have been used as materials of traditional oriental medicine named as 'mihudo', to treat liver disease, gastrointestinal disease and urogenital lithiasis without toxicity (Chung B. S, and Shin M. K.; *HyangyakDaesacheon*, Youngrimsa., pp 386-388, 1998).

Meanwhile, there have been several applications regarding the activity of *Actinidia* fruit to treat or prevent various medicinal diseases till now.

For example, Korea Patent Publication No. 2002-78467 discloses health beverage containing an extract of crude drugs consisting of *Actinidia arguta, Hovenia dulcis, Lycium chinensis, Schizandra chinensis, Artemis capillaries, Puerraria thunbergiana, Glycyrrhiza uralensis, Lagenaria siceraria, Aralia elata, Polygala tenuifolia, Angelica sinensis, Atractylodes macrocephala, Gardenia jasminoides, Astragalus membranaceus, Carthamus tinctorius* and *Cordyceps militaris* for the improvement of liver function.

However, there has been not reported or disclosed an activity of an extract of hardy kiwi for treating or preventing alopecia and seborrheic skin disease in any of above literatures.

To investigate the treating or preventing effect of hardy kiwi extract on alopecia and seborrheic skin disease, the inventors of the invention have intensively carried out in vivo and in vitro experiment concerning the inhibition effect on the reproduction of DHT (dihydrotestosterone) together with clinical experiment concerning on the hair growth stimulation and seborrheic skin disease. As a result of the investigation, the inventors finally confirm that the extract of hardy kiwi reduced blood DHT level, and inhibited the falling out of hair as well as suppressed the severity of seborrheic skin disease.

SUMMARY OF THE INVENTION

The present invention provides a pharmaceutical composition comprising an extract of hardy kiwi as an active ingredient in an effective amount to treat or prevent baldness disorder or seborrheic skin disease.

The present invention provides a use of an extract of hardy kiwi for the preparation of pharmaceutical composition for to preventing or alleviating baldness disorder or seborrheic skin disease in human or mammal.

The present invention also provides a method for treatment, improvement or prevention of baldness disorder or seborrheic skin disease in a mammal comprising administering to said mammal an effective amount of a crude extract, non-polar solvent soluble extract or purified extract of hardy kiwi, together with a pharmaceutically acceptable carrier thereof.

The present invention also provides a health food or food additives comprising an extract of hardy kiwi for improvement or prevention of baldness disorder or seborrheic skin disease.

The present invention also provides a feed or feed additive comprising an extract of hardy kiwi for treatment or prevention of baldness disorder or seborrheic skin disease.

The present invention also provides a cosmetic composition comprising an extract of hardy kiwi as an active ingredient in an effective amount to treat or prevent baldness disorder or seborrheic skin disease.

DISCLOSURE OF THE INVENTION

Accordingly, it is an object of the present invention to provide a pharmaceutical composition comprising a crude extract, non-polar solvent soluble extract or purified extract of hardy kiwi as an active ingredients for treatment or prevention of baldness disorder or seborrheic skin disease.

It is an object of the present invention to provide a use of a crude extract, non-polar solvent soluble extract or purified extract of hardy kiwi for the preparation of a therapeutic agent for treating or preventing baldness disorder or seborrheic skin disease in human or mammal.

It is an object of the present invention to provide a method for treatment, improvement or prevention of baldness disorder or seborrheic skin disease in a mammal comprising administering to said mammal an effective amount of a crude extract, non-polar solvent soluble extract or purified extract of hardy kiwi, together with a pharmaceutically acceptable carrier thereof.

It is another object of the present invention to provide a health food or food additives comprising the above described extract, together with a sitologically acceptable additive for prevention, treatment or improvement of baldness disorder or seborrheic skin disease.

It is still another object of the present invention to provide a feed or feed additive comprising the above described extract as essential components for treatment, prevention, or improvement of baldness disorder or seborrheic skin disease.

It is still another object of the present invention to provide a cosmetic composition comprising the described extract for prevention, treatment or improvement of baldness disorder or seborrheic skin disease.

Above described baldness disorders herein comprise alopecia seniles, alopecia greata and the like.

The term "crude extract" defined herein means "an extract" soluble in water, lower alcohol such as methanol, ethanol, butanol or a mixture thereof, preferably, an organic solvent mixture mixed with water and ethanol.

Preferably, the above described crude extract herein comprises an extract obtained by the step consisting of: extracting hardy kiwi with water, lower alcohol such as methanol, ethanol or butanol and the mixture thereof, preferably, an organic solvent mixture mixed with water and ethanol; filtrating and concentrating the filtrate.

The term "non-polar solvent soluble extract" defined herein means "an extract" soluble in chloroform, ethylacetate, hexane, dichloromethane or ether, preferably, ethylactate.

Above described non-polar soluble extract herein comprises an extract obtained by the step consisting of: extracting hardy kiwi with a non-polar solvent such as chloroform, ethylacetate, hexane, dichloromethane or ether, preferably, ethylactate; filtrating and concentrating the filtrate.

The term "hardy kiwi" defined herein means any of "plants with hairless fruits" belonged to *Actinidia* genus.

Above hardy kiwi may comprise *Actinidia arguta, A. kolomikta* or *A. polygama* (Strik et al., *Journal of the American Pomological Society*, 2006) and may use the fruit, stem, root thereof.

The pharmaceutical composition of the present invention can contain about 0.01 to 50% by weight of the above extract based on the total weight of the composition.

The health food of the present invention comprises above extracts as 0.01 to 95%, preferably 1 to 80% by weight based on the total weight of the composition.

Above health food can be contained in health food, health beverage etc, and may be used as powder, granule, tablet, chewing tablet, capsule, beverage etc.

An inventive extract from hardy kiwi may be prepared in accordance with the following preferred embodiment.

Hereinafter, the present invention is described in detail.

An inventive extract of hardy kiwi can be prepared in detail by following procedures, The inventive crude extract of hardy kiwi can be prepared by follows; hardy kiwi is dried, cut, crushed and mixed with 2 to 25-fold, preferably, approximately 10 fold volume of distilled water, lower alcohols such as methanol, ethanol, butanol and the like, or the mixtures thereof, preferably ethanol; the solution is treated with hot water at the temperature ranging from 20 to 100° C., preferably from 60 to 100° C., for the period ranging from 1 to 24 hours with extraction method by the extraction with hot water, cold water, reflux extraction, or ultra-sonication extraction with 1 to 5 times, preferably 2 to 3 times, consecutively; the residue is filtered to obtain the supernatant to be concentrated with rotary evaporator, at the temperature ranging from 20 to 100° C., preferably from 50 to 70° C. and then dried by vacuum freeze-drying, hot air-drying or spray drying to obtain dried crude extract powder of hardy kiwi which can be soluble in water, lower alcohols, or the mixtures thereof.

Additionally, polar solvent soluble and non-polar solvent soluble extract of present invention can be prepared by following procedure; the crude extract prepared by above step, is suspended in water, and then is mixed with 1 to 100-fold, preferably, 1 to 5-fold volume of non polar solvent such as ethyl acetate, chloroform, hexane and the like; the non-polar solvent soluble layer is collected to obtain non-polar solvent soluble extract of the present invention and remaining polar solvent soluble layer is collected to obtain polar solvent soluble extract of the present invention which is soluble in water, lower alcohols, or the mixtures thereof. Also, above described procedures may be modified or subjected to further step to fractionate or isolate more potent fractions or compounds by conventional procedure well known in the art, i.e., the procedure disclosed in the literature (Harborne J. B. Phytochemical methods: *A guide to modern techniques of plant analysis*, $3^{rd}$ Ed. pp 6-'7, 1998).

For example, the further purified fractions from the extract of hardy kiwi in the present invention can be prepared by subjecting non-polar solvent soluble extract prepared by aforementioned step to column chromatographic process such as Silicagel column chromatography, TLC (Thin layer chromatography) or Sephadex column chromatography, preferably, Silicagel column chromatography eluting with eluting solvent mixed with chloroform:methanol: water in order to increasing their polarity in stepwise manner, more preferably, starting with mixed ratio of 100:10:1 (W/W/W) and ending with 20:10:0.5(W/W/W) to obtain further purified extract, in particular, the purified extracts having TLC spectra as shown in FIGS. 1 to 3.

Accordingly, the present invention to also provide a pharmaceutical composition comprising the crude extract, non-polar solvent soluble extract or purified extract of the hardy kiwi obtained by above described method as an active ingredients for treatment or prevention of baldness disorder or seborrheic skin disease.

It is an object of the present invention to provide a use of the crude extract, non-polar solvent soluble extract or purified extract of hardy kiwi obtained by above described method for the preparation of therapeutic agent for treating or preventing baldness disorder or seborrheic skin disease in human or mammal.

The term "purified extract" defined herein means any of "fractions" obtained by column chromatographic purification having more potent activity than that of polar or non-polar solvent soluble extracts, preferably, the purified extracts having TLC spectra as shown in FIGS. 1 to 3.

To investigate the inhibiting activity of the crude extract, non-polar solvent soluble extracts and purified extracts of hardy kiwi extract prepared by above procedure on the baldness disorder or seborrheic skin disease, in vivo and in vitro experiments concerning the inhibition effect on the reproduction of DHT (dihydrotestosterone) in mouse blood and on the formation of mouse hair root together with clinical experiment concerning on the hair growth stimulation and seborrheic skin disease were carried out. As a result of the investigation, the inventors confirmed that an orally administrated hardy kiwi extract reduced blood DHT level, promoted the formation of hair root in mouse model experiment, and inhibited the falling out of hair and improved seborrheic skin disease of volunteers such as keratic skin, seborrhea etc.

In accordance with another aspect of the present invention, there is provided a pharmaceutical composition comprising the extract of hardy kiwi prepared by above preparation method for the treatment or prevention of baldness disorder or seborrheic skin disease as active ingredients.

It is another of the present invention to provide a treating method or preventing method comprising administering a pharmaceutical composition comprising said extract prepared by above preparation method to human or mammals suffering from baldness disorder or seborrheic skin disease.

The composition for treating or preventing baldness disorder and seborrheic skin disease may comprises above extracts as 0.01 to 50% by weight based on the total weight of the composition.

The inventive composition may additionally comprise a conventional carrier, adjuvant or diluents in accordance with conventional using method well known in the art.

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments or creams.

Pharmaceutical formulations containing the composition of the invention may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to administer at the amount ranging 0.01 to 10 g/kg, preferably, 0.1 to 3 g/kg by weight/day of the inventive extract or compounds of the present invention. The dose may be administered in single or divided into several times per day. In terms of composition, the amount of inventive extract should be present between 0.01 to 95% by weight, preferably 0.5 to 80% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

Also, the present invention provide a composition of the health food beverage for prevention or improvement of baldness disorder or seborrheic skin disease adding the extract of hardy kiwi 0.01 to 20% by weight, amino acids 0.001 to 5% by weight, vitamins 0.001 to 2% by weight, sugars 0.001 to 20% by weight, organic acids 0.001 to 10% by weight, sweetener and flavors of proper amount.

Above the extract of hardy kiwi can be added to food or beverage for the prevention or improvement of baldness disorder or seborrheic skin disease.

To develop for health food, examples of addable food comprising above extracts of the present invention are e.g., various food, beverage, gum, vitamin complex, health improving food and the like, and can be used as power, granule, tablet, chewing tablet, capsule or beverage etc.

Also, the extract of present invention will be able to prevent or improve baldness disorder and seborrheic skin disease by comprising to child and infant food, such as modified milk powder, modified milk powder for growth period, modified food for growth period.

Above described composition therein can be added to food, additive or beverage, wherein, the amount of above described extract in food or beverage may generally range from about 0.1 to 95 w/w %, preferably 1 to 80 w/w % of total weight of food for the health food composition and 1 to 30 g, preferably 3 to 10 g on the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract therein are various food, beverage, gum, vitamin complex, health improving food and the like.

The inventive composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol, catechin, tocopherol, rosemary extract, vitamin C, green tea extract, licorice root extract, chitosan, tannic acid, phytic acid etc.

The above extract of hardy kiwi may be 20 to 90% high concentrated liquid, power, or granule.

Similarly, the above extract of hardy kiwi can comprise additionally one or more than one of lactose, casein, dextrose, glucose, sucrose and sorbitol.

Also, in the present invention, there is also provided a using method of the food additives such as sterilizer, spice, seasoning, various nutrients, vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al, or as essential component of food materials.

Wherein the food additives can be added to food by deposition, spray, or mixing the ratio of the additives is not so important but is generally range from about 0.01 to 20 w/w % per 100 w/w % present composition. Examples of addable food comprising aforementioned extract therein are.

Wherein the food additives can be added to one or one over food such as fruits, vegetables, food dehydrated foods or cutting products such as fruits, vegetables; fruit juice, vegetable juices or the mixture juices thereof; drinks containing acid-beverage; confectionaries such as cookie, candy, caramel, gum; breads; ice creams, teas, fermented milk such as yogurt; dairy product, spices, alcoholic beverages, cans, in-bottles, noodles, processed livestock products, processed marine products, fermented food, beans food, cereals food, processed meats, licorices or hubs.

In accordance with another aspect of the present invention, there are provided a feed or feed additive essentially comprising said extract prepared by above preparation method for prevention or improvement baldness disorder or seborrheic skin disease.

Above food additives of the present invention can be mixed with mixing amount of 5 to 100 g per 1 kg by weight based on the total dried weight of the feed.

Furthermore, the present invention provides a feed composition comprising above feed additives.

Also, the present invention also provides a cosmetic composition comprising an effective amount of the crude extract or non-polar solvent soluble extract of hardy kiwi for prevention or improvement of baldness disorder or seborrheic skin disease.

The present cosmetic composition provide cosmetic composition comprising the above extracts with 0.01 to 30%, more preferably, 0.01 to 5% by the weight of the inventive composition based on the total weight of the composition for the treatment, prevention or improvement of baldness disorder or seborrheic skin disease.

The other components may be a mixture of the ingredients of a conventional cosmetic composition well known in the art.

Cosmetic formulations containing above composition may be prepared in any form such as skin, lotion, cream, essence, toner, emulsion, pack, soup, shampoo, rinse, cleanser, body washing solution, washing solution, treatment, gel, balm, spray solution and the like.

The cosmetic composition of the present invention can comprises additional additives selected from the group consisting of water soluble vitamin, lipid soluble vitamin, peptide polymer, polysaccharide polymer, sphingolipid and seaweed extract.

Preferable water soluble vitamins are any one which can be mixed with cosmetic, however, various vitamin such as vitamin B1, B2, B6, pyridoxine, pyridoxine HCl, vitamin B12, pantothenic acid, nicotinic acid, nicotinamide, folic acid, vitamin C, vitamin H etc, their salt thereof such as thiamin HCl salt, ascorbic acid Na salt etc or their derivatives thereof such as ascorbic acid-2-phosphonic acid Na salt, ascorbic acid-2-phosphonic acid Mg salt are preferable and those can be obtained by conventional method such as microbial conversion method, purification method from the microbial cultivates, enzymatic method or chemical synthetic method.

Preferable lipid soluble vitamins are any one which can be mixed with cosmetic, however, various vitamin such as vitamin A, D2, D3, E (dl-α-tocopherol, d-α-tocopherol, d-δ-tocopherol) and their derivatives such as palmitic acid ascorbate, stearic acid ascorbate, dipalmitic acid ascorbate, acetic acid-dl-α-tocopherol, nicotinic acid dl-α-tocopherol vitamin E, dl-pantothenyl alcohol, D-pantothenyl alcohol, pantothenyl ethylether etc. containing the lipid soluble vitamin used in examples of present invention are preferable and those can be obtained by conventional method such as microbial conversion method, purification method from the microbial cultivates, enzymatic method or chemical synthetic method.

Preferable peptide polymers are any one which can be mixed with cosmetic, however, collagen, hydrolysable collagen, gelatin, elastin, hydrolysable gelatin, keratin etc. containing the peptide polymer used in examples of present invention are preferable.

Preferable polysaccharide polymers are any one which can be mixed with cosmetic, however, hydroxy ethyl cellulose, xanthin gum, hyaluronic acid Na, chondroitin sulfate or their salt (Na salt etc) and the like are preferable. For example, chondroitin sulfate or the salt thereof etc can be used by being purified from mammal or fishes ordinarily.

Preferable sphingolipids are any one, which can be mixed with cosmetic, however, ceramide, pit-sphingosin, sphingo-lipopolysaccharide and the like are preferable. Sphingo-lipid can be obtained by being purified from mammal, fish, shellfish, yeast or plant etc in conventional method.

Preferable seaweed extract is any one which can be mixed with cosmetic, however, the extract of brown algae, red algae, green algae and the like or the purified carrageenan, alginic acid, arginic acid Na, K isolated therefrom are preferable. Algae extract can be obtained by being purified from seaweed in conventional method.

The cosmetic composition of the present invention may combine with other ingredients combined with conventional cosmetic composition, if necessary, together with above described essential ingredient.

The above described other ingredients may comprises oil ingredient, humectants, emollients, surface active agents, organic or inorganic dye, organic powder, ultraviolet ray absorbing agent, preservatives, antiseptics, antioxidants, plant extract, pH controller, alcohol, pigments, perfumes, refrigerants, blood circulator, antihidrotic, distilled water etc.

Preferable oil ingredients may comprise ester oil, hydrocarbon oil, silicone oil, fluoride oil, animal oil, plant oil and so on.

Preferable ester oil described above may comprise glyceryl tri-2-ethyl hexanoic acid, cetyl 2-ethyl hexanoic acid, isopropyl myristic acid, butyl myristic acid, isopropyl palmitic acid, ethyl stearic acid, octyl palmitic acid, isocetyl isostearic acid, butyl stearic acid, ethyl linoleic acid, isopropyl linoleic acid, ethyl oleic acid, isocetyl myristic acid, isostearyl myristic acid, isostearyl palmitic acid, octyldodecyl myristic acid, isocetyl isostearic acid, diethyl sebasic acid, isopropyl adipic acid, isoalkyl neopetanoic acid, glyceryl tri(capryl, capric acid), trimethylopropane tri-2-ethyl hexanoic acid, trimethylopropane triisostearic acid, pentaerythritol tetra-2 ethyl hexanoic acid, cetyl caprylic acid, decyl lauric acid, hexyl lauric acid, decyl myristic acid, myristyl myristic acid, cetyl myristic acid, stearyl stearic acid, decyl oleic acid, cetyl licinoleic acid, isostearyl lauric acid, isotridecyl myristic acid, isocetyl palmitic acid, octyl stearic acid, isocetyl stearic acid, isodecyl oleic acid, octyldodecyl oleic acid, octyldodecyl linoleic acid, isopropyl isostearic acid, cetostearyl 2-ethyl hexanoic acid, stearyl 2-ethyl hexanoic acid, hexyl isostearic acid, ethylene glycol dioctanoic acid, ethylene glycol dioleic acid, propylene glycol dicapric acid, propylene glycol di(capryl, capric acid), propylene glycol dicaprylic acid, neopentylglycol dicapric acid, neopentylglycol dioctanoic acid, glyceryl tricaprylic acid, glyceryl triundecylic acid, glyceryl triisopalmitic acid, glyceryl triisostearic acid, octyldodecyl neopentanoic acid, isostearyl octanoic acid, octyl isononanoic acid, hexyldecyl neodecanoic acid, octyldodecyl neodecanoic acid, isocetyl isostearic acid, isostearyl isostearic acid, octyldecyl isostearic acid, polyglycerin oleanoic acid ester, polyglycerin isostearic acid ester, triisocetyl citric acid, triisoalkyl citric acid, triisooctyl citric acid, lauryl lactic acid, myristyl lactic acid, cetyl lactic acid, octyldecyl lactic acid, triethyl citric acid, acetyltriethyl citric acid, acetyl tributyl citric acid, trioctyl citric acid, diisostearyl maleic acid, di 2-ethylhexyl hydroxy stearic acid, 2-ethyl hexyl succinic acid, diisobutyl adipic acid, diisopropyl sebasinic acid, dioctyl sebacinic acid, cholesteryl stearic acid, cholesteryl isostearic acid, cholesteryl hydroxy stearic acid, cholesteryl hydroxy stearic acid, cholesteryl oleic acid, dihydrocholesteryl oleic acid, pitsteryl isostearic acid, pitsteryl oleic acid, isocetyl 12-stealoyl hydroxy stearic acid, stearyl 12-stealoyl hydroxy stearic acid, isostearyl 12-stealoyl hydroxy stearic acid.

Preferable hydrocarbon oil described above may comprise squalene, liquid paraffin, α-olefin oligomer, isoparaffin, ceresin, paraffin, liquid isoparaffin, polybuden, microcrystalline wax, vaselin and the like.

Preferable silicone oil may comprise polymethylsilicone, methylphenylsilicone, methylcyclopolysiloxane, octamethylpolysiloxane, decamethylpolysiloxane, dodecamethylcyclosiloxane, dimethyl siloxane-methyl cetyloxysiloxan copolymer, dimethyl siloxane-methyl stealoxysiloxane copolymer, alkyl modified silicone oil, amino modified silicone oil and the like.

Preferable fluoride oil can comprise perfluoropolyether and the like.

Preferable animal or plant oil can comprise avocado oil, almond oil, olive oil, sesame oil, rice husk oil, safflower oil, soy-bean oil, corn oil, rape oil, amygdalin oil, palm kernel oil, palm oil, pimaja oil, sunflower oil, fruite seed oil, cotton seed oil, coconut palm oil cucui nut oil, wheat embryo bud oil, rice embryo bud oil, sia butter, evening-primrose oil, marker daymia nut oil, medo home oil, egg yolk oil, lanolin, hempseed oil, mink oil, orange ruppy oil, hohoba oil, carnawa wax, liquid lanolin, solid pimaja wax and the like.

Preferable humectants can comprise water-soluble low molecular humectants, lipophilic low molecular humectants, water-soluble polymer and lipid soluble polymer.

Specifically, preferable water soluble low molecular humectants can comprise cerin, glutamine, sorbitol, mannitol, pyrrolidone-carboxylic acid Na, glycerin, propylene glycol, 1,3-butylene glycol, ethylene glycol, polyethylene glycol (polymerization index >2), polypropylene glycol (polymerization index >2), lactic acid, lactate salt and the like.

Preferable lipid soluble low molecular humectants can comprise cholesterol, cholesteryl ester and the like.

Preferable water-soluble polymer can comprise carboxy vinyl polymer, poly asparaginic acid salt, tragacanth, xanthin gum, HMC (hydroxy methyl celluose), HEC (hydroxy ethyl celluose), HPC (hydroxy propyl celluose), carboxymethylcellulose, water-soluble chitin, chitosan, dextrin and the like.

Preferable lipid soluble polymer can comprise polyvinylpyrrolidone-eicocene copolymer, polyvinylpyrrolidone-hexadecene copolymer, nitrocellulose, dextrin fatty acid ester, silicone polymer and the like.

Preferable emollients can comprise long chain acyl glutamic acid cholesteryl ester, cholesteryl hydroxy stearic acid, 12-hydroxy stearic acid, rogic acid, lanolin fatty acid cholesteryl ester and the like.

Preferable surface-active agent can comprise nonionic surfactants, anionic surfactants, cationic surfactants, ambivalent surfactants and the like.

Specifically, preferable non-ionic surfactants can comprise self-emulsified monostearic acid glycerin, propylene glycol fatty acid ester, glycerin fatty acid ester, polyglycerin fatty acid ester, sorbitan fatty acid ester, polyoxyethylene (POE) sorbitan fatty acid ester, POE sorbitan fatty acid ester, POE glycerin fatty acid ester, POE alkyl ether, POE fatty acid ester, POE solid pimaja oil, POE pimaja oil, POE-POP copolymer, POE-POP alkyl ether, polyether modified silicone, lauric acid alkanol amide, alkyl amine oxide, hydrogen addition soybean phospholipid and the like.

Preferable anionic surfactants can comprise fatty acid soap, α-acyl sulfonic acid salt, alkyl sulfonic acid salt, alkyl ally sulfonic acid salt, alkyl naphthalene sulfonic acid salt, alkyl sulfonic acid salt, POE alkylether sulfate salt, alkyl amide sulfate salt, alkyl phosphate salt, POE alkyl phosphate salt, alkylamide phospahate salt, alkyloylalkyl taurine salt, N-acyl-amino acid salt, POE alkyl ether carboxylic acid salt, alkyl sulfo succinic aid salt, alkyl sulfo-acetic acid salt, acylated hydrolysable collagen peptide salt, perfluoro alkyl phosphate ester and the like.

Preferable cationic surfactant can comprise alkyl trimethyl ammonium chloride, stearyl trimethyl ammonium chloride, stearyl trimethyl ammonium bromide, setostearyltrimethyl ammonium chloride, distearyl dimethyl ammonium chloride, stearyl dimethyl benzyl ammonium chloride, vehenyltrimethyl ammonium bromide, benzalkonium chloride, diethylamino ethyl amide stearic acid, dimethylaminopropyl amide stearic acid, lanolin derivatives quaternary ammonium and the like.

Preferable ambivalent surfactants can comprise carboxy betaine type, amide betaine type, hydroxy sulfo betaine type, phosphpbetaine type, aminocarboxylic acid, imidazoline derivatives type, amide amine type and the like.

Preferable organic and inorganic dyes can comprise silicic acid, anhydrous silicic acid, magnesium silicic acid, talc, ceracyte, mica, caolin, bengala, clay, bentonite, titan film mica, oxy chlorine bismuth, zirconium oxide, magnesium oxide, zinc oxide, titan oxide, aluminium oxide, calcium sulfate, barium sulfate, magnesium sulfate, calcium carbonate, magnesium carbonate, ferrous oxide, chromium oxide, chromium hydroxide, calamine, carbon black and their complex thereof as an inorganic dyes; polyamide, polyester, polypropylene, polystyrene, polyurethane, vinyl resin, urea resin, phenol resin, fluoride resin, silicone resin, acryl resin, melamine resin, epoxy resin, polycarbonate resin, divinyl benzene-styrene copolymer, silk powder, cellulose, CI pigment yellow, CI pigment orange as an organic dyes; and their complex etc.

Preferable organic powder can comprise metal soap such as calcium stearate; alkyl phosphonate metal salt such as sodium zinc cetylic acid, zinc laurylic acid, calcium laurylic acid; acylamino acid polyvalent metal salt such as calcium N-lauroyl-β-alanine, zinc N-lauroyl-β-alanine, calcium N-lauroyl-glycine etc.; amide sulfonic acid polyvalent metal salt such as calcium N-lauroyl-taurine, calcium N-palmitoyl-taurine; N-acyl basic amino acid such as Nε-lauroyl-L-lysine, Nε-palmitoyl-lysine, Nα-palmitoyl ornitine, Nα-lauroly arginine, hardened lanolin fatty acid acyl arginine and the like; N-acylpolypeptide such as N-lauroylglycyl glycine; α-amino fatty acid such as α-amino caprylic acid, α-amino lauric acid and the like; polyethylene, polypropylene, nylon, polymethylmetacrylate, polystyrene, divinylbenzene-styrene copolymer, ethylene tetrafluoride and so on.

Preferable ultraviolet absorbing agents can comprise paraminobenzoic acid, paraamonoethyl benzoate, paramino amyl benzoate, paramino octyl benzoate, ethyleneglycol salicylate, phenyl salicylate, octyl salicylate, benzyl salicylate, butylphenyl salicylate, homomentyl salicylate, benzyl cinnamic acid, paramethoxy 2-ethoxy ethyl cinnamic acid, paramethoxy octyl cinnamic acid, diparamethoxy mono-2-ethylhexane glyceryl cinnamic acid, paramethoxy isopropyl cinnamic acid, diisopropyl-diisopropyl cinnamate ester mixture, urokanic acid, ethyl urokanic acid, hydroxy methoxy benzophenone, hydroxymethoxy benzophenone sulfonic acid and their salt, dihydroxy methoxy benzophenone, dihydroxy methoxy benzophenone disulfonate Na, dihydroxy benzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl) benzotriazole and the like.

Preferable preservatives can comprise hinokitiol, trichloric acid, trichlorohydroxydiphenylether, chlorohexidine glucuronate, phenoxyethanol, resorcine, isopropylmethylphenol, azulene, salicylic acid, zinc pilithione, bezalconium HCl, photosensitizer 301, mononitroguaiacol Na, undecylenic acid etc.

Preferable antioxidants can comprise butylhydroxyanisole, propyl gallate, ellisorbate and the like.

Preferable pH controller can comprise citric acid, sodium citrate, malic acid, sodium malate, fumaric acid, sodium fumaric acid, succinic acid, sodium succinic acid, sodium hydroxide, sodium hydrogen phosphate and the like.

Preferable alcohol can comprise cetyl alcohol etc.

Furthermore, other ingredient addable to above described component and the amount thereof is not limited within the scope of the purpose and effect of the present invention, however, it is preferable that the amount of the other ingredients ranges from 0.01 to 5%, more preferably, 0.01 to 3% in that of total composition.

The cosmetic composition of the present invention can be modified as a solution, emulsion, cohesive mixture etc.

Above described ingredients such as water-soluble vitamin, lipid soluble vitamin, peptide polymer, polysaccharide polymer, sphingolipid, sea weed extract and addable ingredients which can be added other than above described ingredients if necessary, can be obtained by conventional methods disclosed in the literature (Matsumoto Mithio, *Manual for the development of transdermal applied preparation*. Seisi Press, 1$^{st}$ Ed., 1985).

Additionally, the present invention also provides a cosmetic additives comprising above described extract as an essential component for prevention or improvement of baldness disorder and seborrheic skin disease.

Above cosmetic additives can be used by adding to existing cosmetics and washing solution to prevent, improve or treat baldness disorder and seborrheic skin disease.

Furthermore, above cosmetic additives can be used to cream, lotion, message pack, and body washing solution, soup, shampoo and the like.

Inventive extract of the present invention have no toxicity and adverse effect therefore; they can be used with safe.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

BRIEF DESCRIPTION OF THE DRAWINGS

The above and other objects, features and other advantages of the present invention will more clearly understood from the following detailed description taken in conjunction with the accompanying drawings, in which.

BEST MODE FOR CARRYING OUT THE INVENTION

Figure 1:
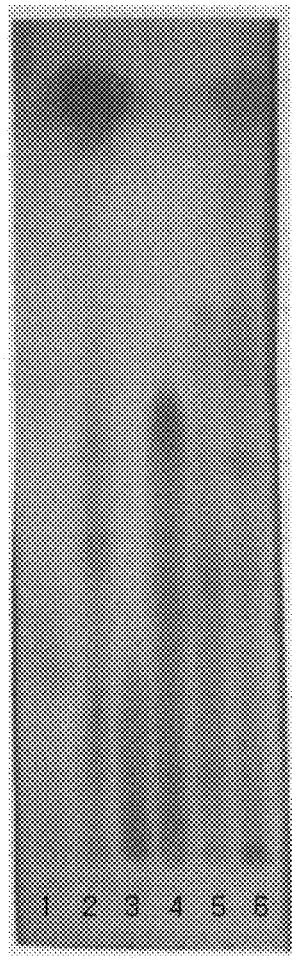
FIG. 1 shows TLC photograph of the extracts and fractions of hardy kiwi.

The following Examples and Experimental Examples are intended to further illustrate the present invention without limiting its scope.

Example 1

Preparation of Hardy Kiwi Extract 1-1. Preparation of Water Extract of Hardy Kiwi 100 g of dried fruit and dried stem of *Actinidia arguta*, dried fruit of *A. kolomikta*, and dried fruit of *A. polygama* purchased from Kyung-dong Market located in Seoul were crushed, mixed with 1 L of distilled water and subjected to reflux extraction for 3 hrs at 90~95° C. with three times and the extract was filtered with filter paper, concentrated using by rotary evaporator (N-1000, Eyela Co. Japan) at 55~65° C. under reduced pressure and dried with freezing dryer to obtain 15.6 g of dried fruit extract of *Actinidia arguta*, 10.4 g of dried stem extract of *Actinidia arguta*, 16.2 g of dried fruit extract of *A. kolomikta* and 17.0 g of dried fruit extract of *A. polygama*. The powdered extract was dissolved in distilled water (100 mg/ml) separately.

1-2. Preparation of Water-Alcohol Soluble Extract of Fruit of Hardy Kiwi

Except using various ratios of a water-alcohol solvent mixture such as 30%, 50%, and 70% ethanol in water as an extraction solvent, in place of water, all the procedure was identical to those of Example 1-1. As a result, 11 g ~13 g of dried extract of fruit of *Actinidia arguta* were obtained at each ratio of the solvent mixtures and the each powdered extract was dissolved in distilled water (100 mg/ml).

Example 2

Preparation of Polar Solvent and Non-Polar Solvent Soluble Hardy Hardy Kiwi Extract The water extract of dried fruit of *Actinidia arguta* prepared in Example 1-1 was subject to fractionation by following procedure.

2-1. Preparation of Chloroform Soluble Fraction 50 ml of distilled water was added to 5 g of the fruit extract of *Actinidia arguta* obtained in Example 1-1. 50 ml of chloroform was added thereto in separatory funnel, shaken vigorously to divide into chloroform soluble layer and water soluble layer I.

2-2. Preparation of Ethyl Acetate Soluble Fraction

Above water soluble layer I obtained in Example 2-1 was mixed with 50 ml of ethyl acetate and then divided into ethyl acetate soluble layer and water soluble layer II.

Above chloroform soluble layer, ethyl acetate soluble layer and water soluble layer II were concentrated by rotary evaporator, dried with freeze dryer to obtain 0.34 g of chloroform soluble fraction, 0.05 g of ethyl acetate soluble fraction, and 4.61 g of water fraction powders, respectively.

Example 3

Fractionation of Hardy Kiwi Extract by Silica Gel Column Chromatography 2,784 mg of ethyl acetate soluble fraction in Example 2-2 was further subjected to silica gel column chromatography (Daiso gel IR-60-W-40: 63 mm). The developing solvent was started with chloroform:methanol:water ([1] 90:11:1, [2] 60:10:1, [3] 60:20:2) solvent mixture and ended with methanol[4] with eluting speed of 300 ml/hr to obtain four sub-fractions([1] 2,381 mg, [2] 135 mg, [3] 148 mg, [4] 98 mg).

Above water extract, ethyl acetate soluble fraction and four sub-fractions were subjected to TLC (TLC plate: Merck Co. Ltd., Developing solvent; chloroform: methanol: water=9:5:1) and the results were shown in FIG. 1. As shown in FIG. 1, lane 1 is water extract, lane 2 is ethyl acetate soluble fraction, lane 3 is sub-fraction No.[4], lane 4 is sub-fraction No.[4], lane 5 is sub-fraction No.[2] and lane 6 is sub-fraction No.[1].

Figure 2:
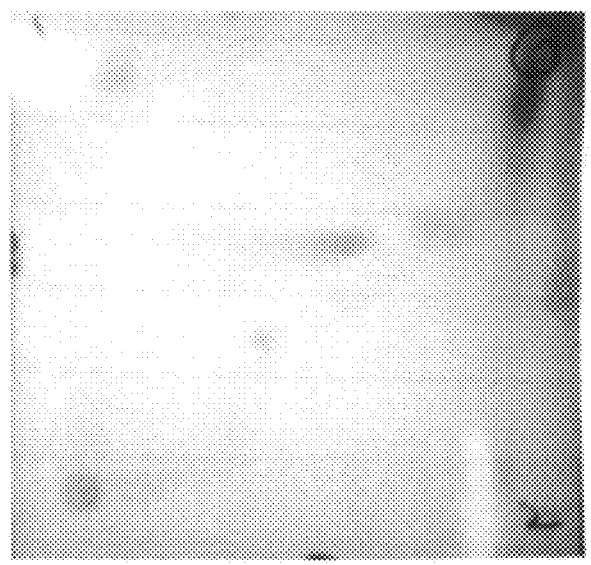
FIG. 2 shows 2D-TLC photograph of [1] sub-fraction.
Figure 3:
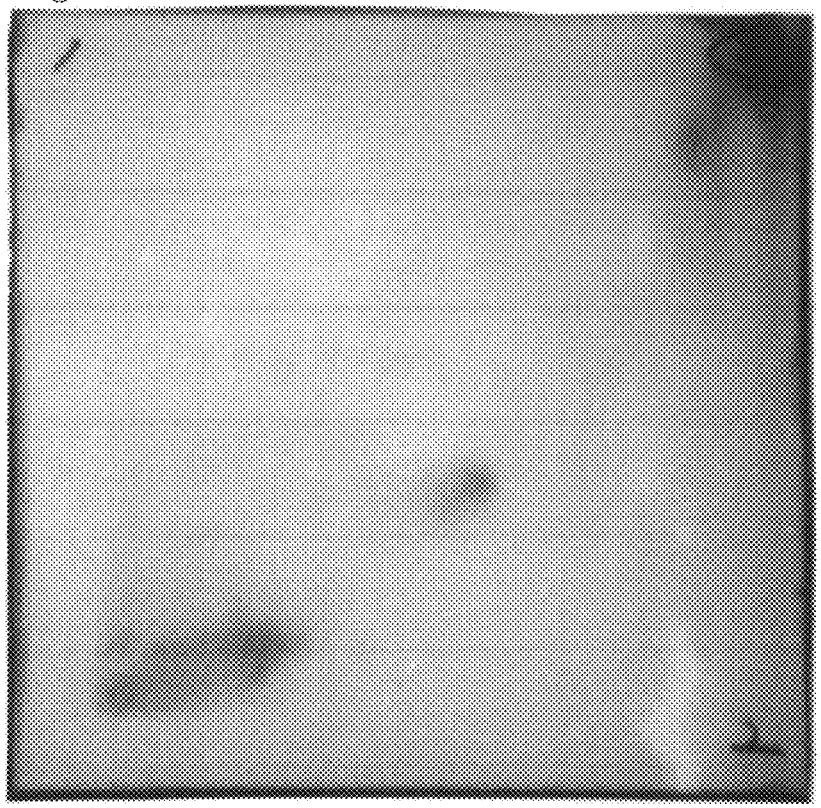
FIG. 3 shows 2D-TLC photograph of [2] sub-fraction.

Above sub-fractions No.[1] and No.[2] were subjected to 2D-TLC using chloroform:methanol:water (9:5:1) solvent mixture as a $1^{st}$ developer and chloroform: acetone:water (3:8:0.5) solvent mixture as a $2^{nd}$ developer (See FIG. 1 and FIG. 2).

Experimental Example 1

Inhibiting Activity on the Formation of Blood DHT

1-1. Effect of Polar Soluble Extract of Hardy Kiwi on the Concentration of Blood DHT To confirm the inhibition effect of hardy kiwi extract on the concentration of blood DHT, the water extract and ethanol extract of fruit of *Actinidia arguta* were administrated into mice and the concentration of blood DHT were determined by following procedure;

Male C57BL/6 mice, aged 6 weeks (Seoul national university animal experimental center) were acclimated to the environment for 1 week. After 1 week, 16 mice were divided into 4 groups and each group was orally administered with 100 µl of the water extract of fruit of *Actinidia arguta* (1500 µg/mouse/day), 100 µl of the ethanol extract of fruit of *Actinidia arguta* (1500 µg/mouse/day), 100 µl of finasteride (100 µg/mouse/day), and 100 µl of drinking water (100 µg/mouse/day) for 3 weeks, respectively. After mice were sacrificed and the blood serum and spleen organ were collected therefrom, the concentration of blood DHT was measured by ELISA (IBL-Hamburg GmbH) method.

Figure 4:
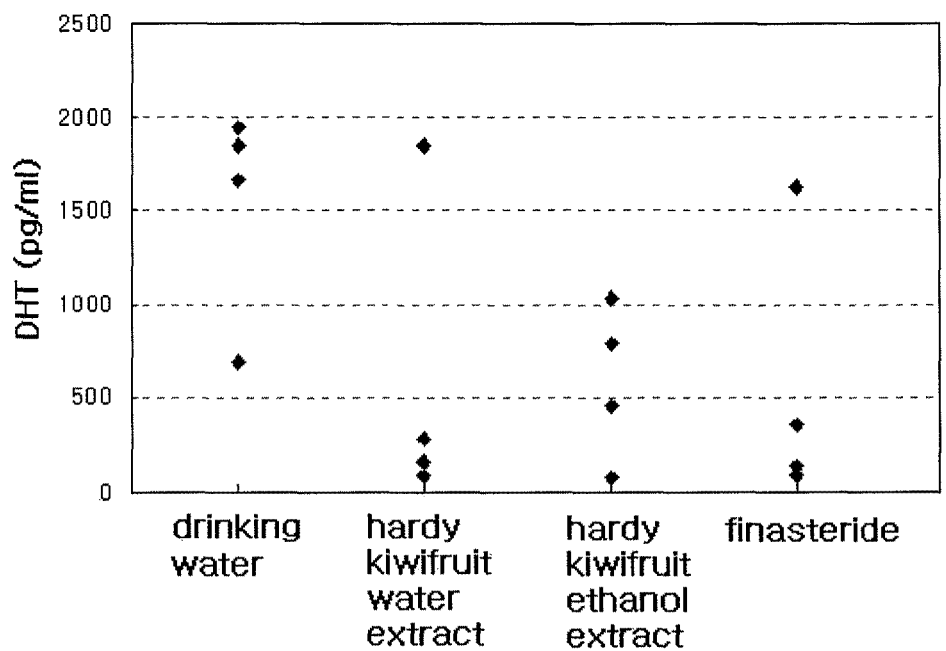
FIG. 4 presents the lowering effect of hot-water extract of hardy kiwi on the blood DHT concentration in mouse.

As shown in the FIG. 4, the concentration of blood DHT in groups administered with extracts of fruit of *Actinidia arguta* showed a decrease of about 90% with similar to groups administered with finasteride.

1-2. Effect of Non-Polar Soluble Extract of Hardy Kiwi on the Concentration of Blood DHT To measure the concentration of blood DHT of C57BL/6 mice, each chloroform soluble fraction, ethyl acetate soluble fraction and water soluble fraction II prepared in above Example 2 was subjected to the identical experiment disclosed in above Experimental Example 1-1.

50 µg of the chloroform soluble fraction, ethyl acetate soluble fraction, or water soluble fraction was administrated to C57BL/6 mice, separately. 100 µl of drinking water was administrated as control.

Figure 5:
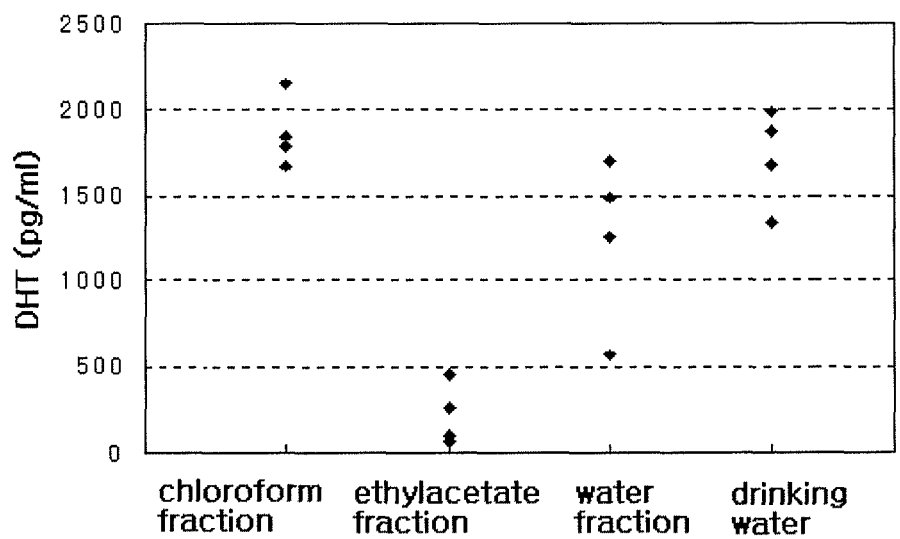
FIG. 5 presents the lowering effect of non-polar solvent soluble extract of hardy kiwi on the blood DHT concentration in mouse.

As shown in the FIG. 5, the concentration of blood DHT showed a decrease by about 95% in the group administered with the ethyl acetate soluble fraction from the extract of *Actinidia arguta* fruit and a slight decrease in the group administered with the water soluble fraction from the extract of *Actinidia arguta* fruit. However, it was not affected in the group administrated with the chloroform soluble fraction of hardy kiwifruit.

1-3. Effect of Silica Gel Column Chromatography-Purified Fraction on the Concentration of Blood DHT To measure the concentration of blood DHT of C57BL/6 mice, each of silica gel column chromatography-purified fractions [1], [2], [3] and [4] prepared in above Example 3 were subjected to the identical experiment disclosed in above Experimental Example 1-1.

Each of 30 µg of silica gel column chromatography fractions [1], [2], [3], or [4] was administrated to C57BL/6 mice, respectively. 100 µl of drinking water was administrated as control.

Figure 6:
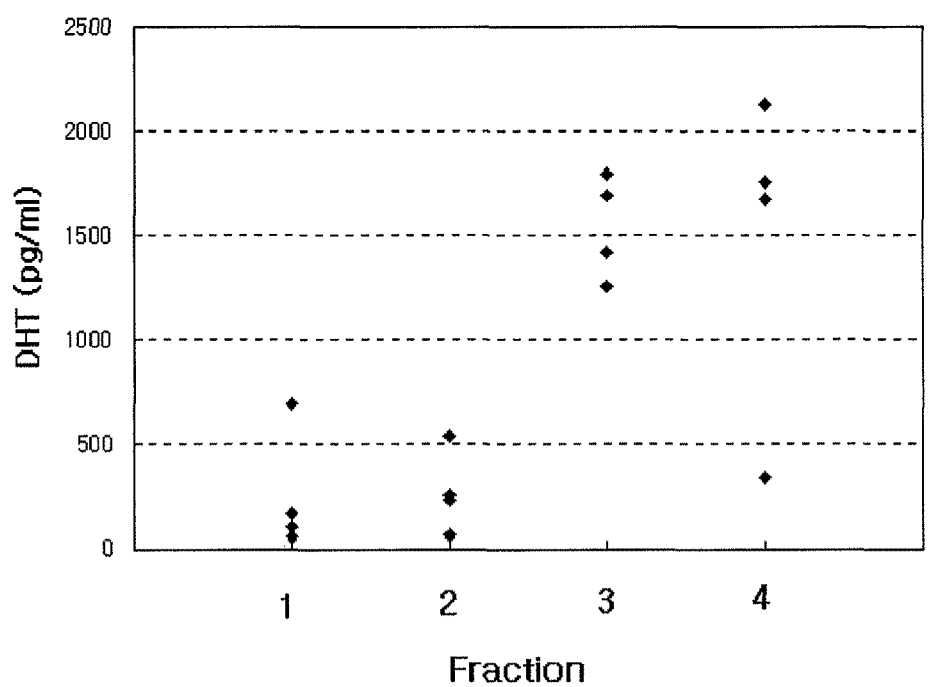
FIG. 6 presents the lowering effect of purified extract of hardy kiwi on the blood DHT concentration in mouse.

As shown in the FIG. 6, mouse administered with fraction [1] and [2] shows significantly inhibition of DHT.

1-4. Effect of Water Extract of Hardy Kiwi Stem on the Concentration of Blood DHT To measure the concentration of blood DHT of C57BL/6 mice, water extract of dried stem of *Actinidia arguta* was subjected to the identical experiment disclosed in above Experimental Example 1-1.

After 1 week, 8 mice were divided into 2 groups and each group was orally administered with 100 µl of the water extract of dried stem of *A. arguta* (1500 µg/mouse/day) and 100 µl of drinking water (100 µg/mouse/day) for 3 weeks, respectively. After mice were sacrificed and the blood serum and spleen organ was colllected therefrom, the concentration of blood DHT was measured. In the group administered with the water extract of dried stem of *A. arguta*, the concentration of blood DHT was 142 µg/ml, 193 µg/ml, 362 µg/ml and 1625 µg/ml, respectively. Therefore, it confirmed that the extract of dried stem of *A. arguta* as well as the extract of dried fruit of *A. arguta* showed an inhibition effect on DHT formation.

Experimental Example 2

Stimulation Effect on the Formation of Hair Root

2-1. Effect of Water Extract of Hardy Kiwi on the Formation of Hair Root

To confirm the effect of water extract of hardy kiwi on the formation of hair root, mouse model was used as follows;

Female C57BL/6 mice aged 6 weeks (Seoul national university animal experimental center) were acclimated to the environment for 7 days. After 1 week, the hair on the back of each mouse was carefully shaved using electrical shaver. Then mice were divided into 2 groups and each group was orally administered with 100 µl of the water extract of fruit of *Actinidia arguta* (1500 µg/mouse/day) and 100 µl of drinking water (100 µg/mouse/day) for 4 weeks, respectively. Whether hair root was activated or not can be easily recognized by confirming the change of skin color where the hair was removed from bright red to darkened color by melanin pigment. Also, the growth of hair can be determined by observing directly the effect of water soluble extract of hardy kiwi on the formation of hair root.

Figure 7:
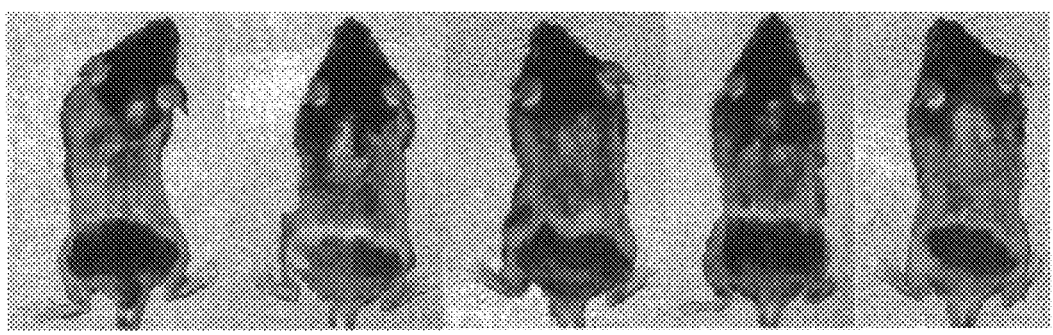
FIGS. 7 and 8 show the photographs of mouse hair grown in its back area treated with control and the hardy kiwi extract for two weeks orally respectively.
Figure 8:
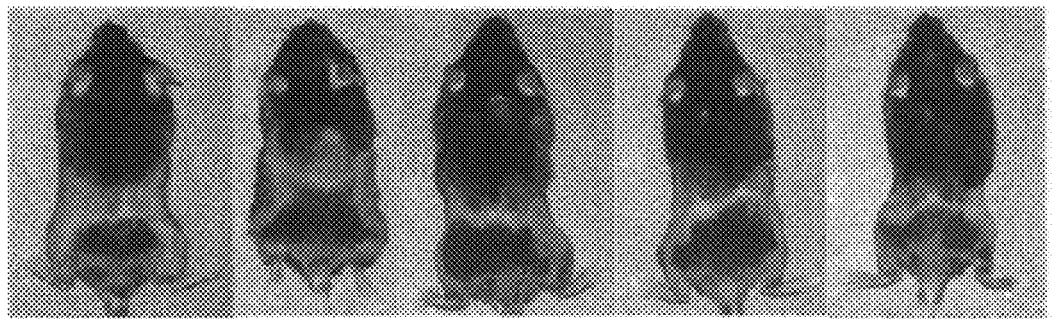

As shown in the FIGS. 7 and 8, the skin color of hair-removed region in the group administered with the water extract of hardy kiwi, got darken within 2 weeks after the administration, which showed the growing of hair. However, the growth of hair as well as the change of skin color did not showed in the group administrated with drinking water. At the time of 4 weeks after administration, the back of each mouse in the former group was covered with new hair, while that in the latter group did not showed any new hair yet. Therefore, it confirmed that the water extract of fruit of hardy kiwi can stimulate hair growth in the mechanism of promoting the formation of hair root of mouse.

2-2. Effect of Non-Polar Solvent Soluble Extract of Hardy Kiwi on the Formation of Hair Root To confirm the effect of chloroform soluble fraction, ethyl acetate soluble fraction and water soluble fraction which were prepared in above Example 2, following experiments were subjected in similar procedure to that disclosed in above Experimental Example 2-1.

Then mice were divided into 4 groups and each group was orally administered with 100 µl of the water soluble layer II of hardy kiwi, 100 µl (50 µg) of the ethyl acetate fraction of hardy kiwi, 100 µl of the chloroform fraction of hardy kiwi or 100 µl of drinking water for 4 weeks.

At the result, hair growth was stimulated significantly in the group administered with the ethyl acetate fraction of hardy kiwi compared with those in the other groups.

Experimental Example 3

Effect of Hardy Kiwi Extract on the Improvement of Seborrheic Skin Disorders

To test the effect of hardy kiwi extract on the improvement of seborrheic skin disorders, each 1 g of water extract of fruit of *Actinidia arguta* was administered orally once a day for 4 weeks to three volunteers suffered from seborrheic dermatitis to confirm whether the seborrheic skin disorder was improved or not as follows:

3-1. Patient K, a 29 year-old Korean female who had been suffered from severe skin seborrheication and lots of dandruffs to progress to depilation. After she had taken tablets containing 1 g of hardy kiwi water extract once a day for 2 weeks, the seborrheic and keratogenous skin disorders was significantly reduced and the depilation syndrome were reduced to more than about 50%.

3-2. Patient P, a 27 year-old Korean male who had been suffered from oily face and scalp and lots of dandruffs. After he had taken tablets containing 1 g of hardy kiwi water extract once a day for 2 weeks, the oily face was significantly alleviated and the alopecia was reduced to more than about 70%.

3-3. Patient U, a 29 year-old Korean male who had been suffered from seborrheic skin, especially, face and purutitic and spotty scalp from several years ago. After he had taken tablets containing 1 g of hardy kiwi water extract once a day for 2 weeks, the purutitic syndrome of scalp was disappeared and the trouble caused by oily face, for example, pimple, was also disappeared significantly.

Experimental Example 4

Effects of Extracts from *A. arguta, A. kolomikta* and *A. polygama* on the Production of IL-4 in RBL-2H3 Cells It is known that lymphocytes from patients with seborrheic skin disorder produce more TH2-type cytokines than TH1-type cytokines (Neuber et al., *Arch. Dermatol. Res.*, pp 532-536, 1996; Ashbee et al., *Exp. Dermatol.*, pp 106-112, 1994; Bergbrant et al., *Clin. Exp. Dermatol.*, pp 402-406, 1999; Parry and Sharpe, *Br. J. Dermatol.*, pp 254-263, 1998; Bergbrant et al., *Clin. Exp. Dermatol.*, pp 331-338, 1991). Among TH2-type cytokines, IL-4 was known to increase a production level in skin lesions from SD patients (Faergemann et al., *Br. J. Dermatol.*, pp 549-556, 2001). Also IL-4 was known to induce apoptosis in cultured human follicular keratinocytes and inhibit hair growth (Mandt et al., *Eur. J. Dermatol.*, pp 432-438, 2002).

To compare the effect of hardy kiwi extracts on the production of IL-4, A23187-stimulated RBL-2H3 cells were used as follows;

RBL-2H3 (Rat mast cell line, ATCC No: CRL-2256) were cultured in 24 well plates in MEM supplemented with 10% FBS, 2 mM L-glutamine, 10 mM HEPES, 1 mM sodium pyruvate, 50 µg streptomycin, and 100 U/ml penicillin (all from Life Technologies, USA) at 37° C. under 5% $CO_2$. Cells were treated with A23187 (1 µg/ml, Sigma, USA) and *A. arguta, A. kolomikta* or *A. polygama* extracts (1 mg/ml). After 12 hrs culture, the supernatants were collected to measure the level of IL-4 by ELISA (rat IL-4 ELISA kit, R&D systems, USA) and the results were expressed as percentage of inhibitory activity on A23187-mediated IL-4 production.

Figure 9:
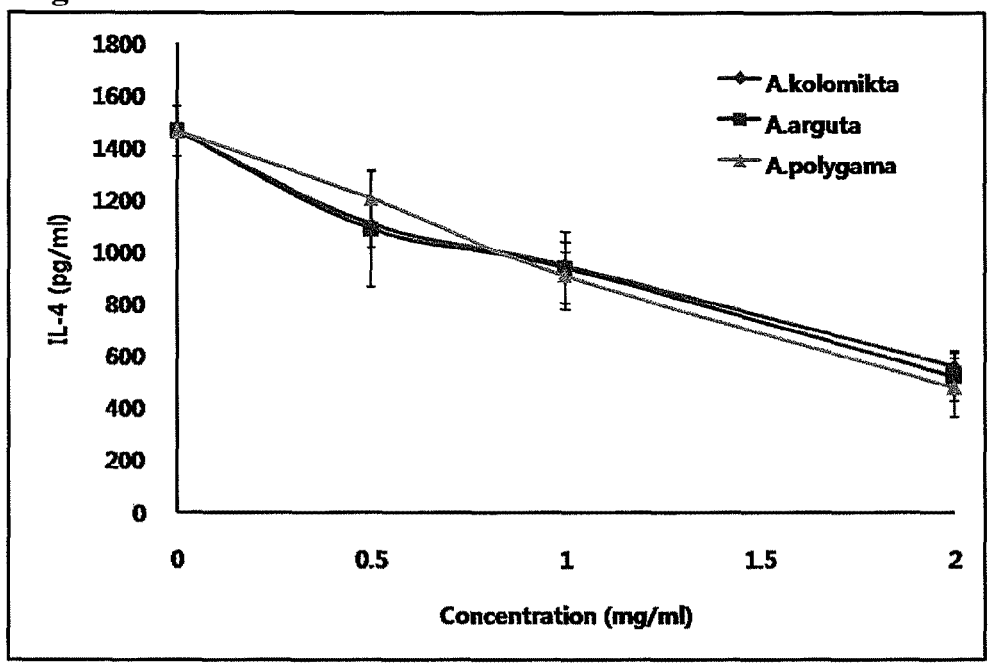
FIG. 9 shows effects of extracts of hardy kiwi on the production of IL-4 in RBL-2H3 cells.

As shown in FIG. 9, the extract of *A. arguta, A. kolomikta* and *A. polygama* decreased the A23187-mediated production of IL-4 in dose-dependent manners. But there was no difference of extracts on reduction of IL-4.

Experimental Example 5

Toxicity Test

To examine the toxicity of the extract of hardy kiwi, repetitive toxicity tests were performed on mouse.

The female of Balb/c mice were divided with 2 groups and inventive water extract of *Actinidia arguta* fruit (150 mg/kg) was administered to the mice at 150 mg/kg for 4 weeks and water was treated to the control group. The symptom of toxicity was observed for 4 weeks such as the change of weight, the hematological analysis and histological test.

As a result of experiment, there was no death example of the mice administered with 150 mg/kg inventive hardy kiwi extract and there was no significant abnormality in the gain or loss of weight, the caloric intake of feed, the hematological analysis and the histological test etc. In accordance with above results, it was confirmed that the hardy kiwi extract was safe to take orally as a medicine.

(1) Weight and observation: the unusual change of weight was not observed.
(2) Hematological analysis: No abnormal symptom was observed in the number of WBC, lymphocyte, monocyte, neutrophil, eosinophil, basophil, RBC, hemoglobin and platelet.
(3) Serum biochemical test: No abnormal symptom was observed in the level of AST, ALT, LDH, bilirubin, creatinine, glucose, cholesterol, minerals, albumin, BUN, lipase and amylase of serum.
(4) Histological test: No abnormal symptom was observed in the tissue of kidneys, the spleen, the liver and the thymus.

Hereinafter, the formulating methods and kinds of excipients will be described, but the present invention is not limited to them. The representative preparation examples were described as follows.

| Preparation of injection | |
|---|---|
| Water extract of hardy kiwi in Example 1 | 50 mg |
| Sodium metadisulfite | 3.0 mg |
| Methylparaben | 0.8 mg |
| Propylparaben | 0.1 mg |
| Distilled water for injection | optimum amount |

Injection preparation was prepared by mixing above components and making 2 ml by the conventional method and then filing filling all the components 2 ml ample and sterilizing by conventional injection preparation method.

| Preparation of tablet | |
|---|---|
| Water extract of hardy kiwi in Example 1 | 50 mg |
| Corn Starch | 100 mg |
| Lactose | 100 mg |
| Magnesium Stearate | 2 mg |

Tablet preparation was prepared by mixing above components and entabletting.

| Preparation of capsule | |
|---|---|
| Water extract of hardy kiwi in Example 1 | 100 mg |
| Corn starch | 100 mg |
| Lactose | 100 mg |
| Talc | 2 mg |
| Magnesium Stearate | optimum amount |

Tablet preparation was prepared by mixing above components and filling gelatin capsule by conventional gelatin preparation method.

| Preparation of liquid | |
|---|---|
| The 70% ethanol extract of hardy kiwi | 100 mg |
| Sugar | 20 g |
| Fructose | 20 g |
| Lemon flavour | optimum amount |
| Distilled water | 100 ml |

Liquid preparation was prepared by mixing above components and then filling 100 ml brown bottle sterilizing by conventional liquid preparation method. Preparation of Health Care Food

| Preparation of health care food | |
|---|---|
| Water extract of hardy kiwi in Example 1 | 1000 mg |
| Vitamin mixture | 20 g |
| Vitamin A acetate | 70 µg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 µg |
| Vitamin C | 10 mg |
| Biotin | 10 µg |
| Amide nicotinic acid | 1.7 mg |
| Folic acid | 50 µg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonates | 100 mg |
| Magnesium chloride | 24.8 mg |

The above-mentioned vitamin and mineral mixture may be varied in many ways. Such variations are not to be regarded as a departure from the spirit and scope of the present invention.

| Preparation of health beverage | |
|---|---|
| Water extract of hardy kiwi in Example 1 | 1000 mg |
| Citric acid | 100 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 2000 ml ample and sterilizing by conventional health beverage preparation method.

| Preparation of skin lotion | |
|---|---|
| Water extract of hardy kiwi in Example 1 | 1.00(%) |
| Glycerol | 3.00 |
| Ethanol | 1.00 |
| Propylene glycol | 0.10 |
| Flavour | trace amount |
| Distilled water | made to 100% |

Skin preparation was prepared by dissolving active component according to conventional lotion preparation method.

| Preparation of lotion | |
|---|---|
| Water extract of hardy kiwi in Example 1 | 3.00(%) |
| L-ascorbic acid-2-magnesium phosphate | 1.00 |
| Soluble collagen (1% solution) | 1.00 |
| Sodium citric acid | 0.10 |
| Citric acid | 0.05 |
| 1,3-butylene glycol | 3.00 |
| Distilled water | made to 100% |

Lotion preparation was prepared by dissolving active component according to conventional lotion preparation method.

| Preparation of cream | |
|---|---|
| Water extract of hardy kiwi in Example 1 | 3.00(%) |
| Polyethyleneglycomonosterate | 2.00 |
| Monostearate glycerin | 1.00 |
| Cetyl alcohol | 4.00 |
| Squalene | .00 |
| Tri 2- glyceryl ethylhexanoate | 6.00 |
| Sphingo-glycolipid | 1.00 |
| 1,3-butylene glycol | 7.00 |
| Distilled water | made to 100% |

| Preparation of pack | |
|---|---|
| Water extract of hardy kiwi in Example 1 | 5.00(%) |
| Polyvinyl alcohol | 13.00 |
| L-ascorbic acid-2-magnesium phosphate | 1.00 |
| Lauroylhydroxyproline | 1.00 |
| Soluble collagen (1% solution) | 2.00 |
| 1,3-butylene glycol | 3.00 |
| Ethanol | 5.00 |
| Distilled water | made to 100% |

Pack preparation was prepared by dissolving active component according to conventional pack preparation method.

| Preparation of beauty solution | |
|---|---|
| Water extract of hardy kiwi in Example 1 | 2.00(%) |
| Hydroxyethylenecellulose (2% solution) | 12.00 |
| Xanthin gum (2% solution) | 2.00 |
| 1,3-butylene glycol | 3.00 |
| Conc. Glycerin | 4.00 |
| Sodium hyaluronate | 5.00 |
| Distilled water | made to 100% |

Beauty solution preparation was prepared by dissolving active component according to conventional beauty solution preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims

INDUSTRIAL APPLICABILITY

As described in the present invention, an extract of the hardy kiwi prepared by inventive preparation reduced blood DHT level, promoted the formation of hair root in mouse model experiment, and inhibited the falling out of hair and improved seborrheic skin disease of volunteers such as keratigenous skin, seborrhea etc. Accordingly, the extract of hardy kiwi can be used as a pharmaceutical composition for the treatment, improvement or prevention of baldness disorder or seborrheic skin disease. Furthermore, an extract of the hardy kiwi can be used as a form of heath care food, food additives, feed additives or cosmetic composition.

What is claimed is:

1. A method for treating or improving seborrheic skin disease or stimulating hair growth comprising orally administering, to a mammal in need thereof, an effective amount of either a) a water extract of *Actinidia arguta* fruit, wherein said water extract is in the form of a granule, powder, pill, sachet or capsule and wherein said sachet or capsule comprises said water extract in the form of granules or powder or b) an ethyl acetate soluble fraction of the water extract of *Actinidia arguta* fruit.

2. The method according to claim 1, wherein said method comprises orally administering a pharmaceutical composition comprising 0.01 to 50% of said water extract of *Actinidia arguta* fruit or said ethyl acetate soluble fraction of the water extract of *Actinidia arguta* fruit.

3. A method for treating or improving seborrheic skin disease or stimulating hair growth comprising orally administering, to a mammal in need thereof, an effective amount of an extract of *Actinidia arguta* fruit, wherein said extract is prepared by:
   a. collecting the ethyl acetate soluble fraction of a water extract of *Actinidia arguta* fruit,
   b. adding the ethyl acetate soluble fraction of part (a) above, to a silica gel chromatography column,
   c. eluting the silica gel column with a mixture of chloroform, methanol and water at a ratio of 90:11:1 and collecting a first fraction eluted,
   d. after step c, eluting said column with a mixture of chloroform, methanol and water at a ratio of 60:10:1 and collecting a second fraction eluted; wherein,
   said extract of *Actinidia arguta* fruit is the first fraction or the second fraction.

4. The method according to claim 3, wherein said method comprises orally administering a pharmaceutical composition comprising 0.01 to 50% of said first or said second fraction.

5. The method of claim 1 or claim 3, wherein said mammal is a human.

* * * * *